(12) United States Patent
Ma

(10) Patent No.: US 8,512,301 B2
(45) Date of Patent: Aug. 20, 2013

(54) CANNED VACUUM

(76) Inventor: Feng Ma, Houston, TX (US)

( * ) Notice: Subject to any disclaimer, the term of this patent is extended or adjusted under 35 U.S.C. 154(b) by 773 days.

(21) Appl. No.: 10/906,199

(22) Filed: Feb. 8, 2005

(65) Prior Publication Data

US 2006/0178649 A1 Aug. 10, 2006

(51) Int. Cl.
*A61M 1/00* (2006.01)
(52) U.S. Cl.
USPC .......................................... 604/319; 604/313
(58) Field of Classification Search
USPC ................. 604/319–321, 331, 348; 4/144.3
See application file for complete search history.

(56) References Cited

U.S. PATENT DOCUMENTS

| | | | | |
|---|---|---|---|---|
| 137,214 A * | 3/1873 | Knight et al. | | 4/144.3 |
| 3,721,243 A * | 3/1973 | Hesterman et al. | | 604/67 |
| 4,121,306 A * | 10/1978 | Bringman et al. | | 600/575 |
| 4,202,058 A * | 5/1980 | Anderson | | 4/144.3 |
| 4,360,933 A * | 11/1982 | Kimura et al. | | 4/301 |
| 4,522,623 A * | 6/1985 | Lauterjung | | 604/319 |
| 4,994,051 A * | 2/1991 | Walsh | | 604/349 |
| 5,073,172 A * | 12/1991 | Fell | | 604/319 |
| 5,356,398 A * | 10/1994 | Willis | | 604/321 |
| 5,520,671 A * | 5/1996 | Bouser | | 604/353 |
| 5,569,225 A * | 10/1996 | Fleury | | 604/323 |
| 5,894,608 A * | 4/1999 | Birbara | | 4/144.3 |
| 6,021,531 A * | 2/2000 | Kirko | | 4/144.3 |
| 6,296,627 B1 * | 10/2001 | Edwards | | 604/347 |
| 6,311,339 B1 * | 11/2001 | Kraus | | 4/144.3 |
| D478,164 S * | 8/2003 | Wang | | D24/108 |
| 6,648,862 B2 * | 11/2003 | Watson | | 604/319 |
| 6,685,681 B2 | 2/2004 | Lockwood | | |
| 6,706,027 B2 * | 3/2004 | Harvie | | 604/347 |
| 6,723,078 B1 * | 4/2004 | Pennington et al. | | 604/327 |
| 6,904,621 B2 * | 6/2005 | Otto et al. | | 4/144.1 |
| 2004/0064132 A1 * | 4/2004 | Boehringer et al. | | 604/543 |

OTHER PUBLICATIONS

PCT International Search Report.

* cited by examiner

Primary Examiner — Melanie Hand

(57) ABSTRACT

An apparatus includes a vacuum container for maintaining a built-in vacuum pressure, and a vacuum device for connecting the vacuum container with a surface. A method to treat patients using a disposable vacuum source is also provided, including applying the disposable vacuum apparatus to the patient's skin, equalizing the pressure in the vacuum apparatus and the pressure on the skin to apply a vacuum suction force, and releasing the vacuum suction force by equalizing the pressure on the skin with the ambient atmospheric pressure.

10 Claims, 2 Drawing Sheets

CANNED VACUUM

BACKGROUND

Conventional urine collection devices have focused on bed-confined patients. A catheter is often used. Some patents cited in the following paragraphs have attempted to use adult diapers, or specially designed funnels and containers to collect urine, but their discomfort and inconvenience are obvious. We summarize conventional urine collection devices as follows:

A. Garments for fixing a urine bag on the body of a user. In U.S. Pat. No. 5,935,116, Kristensen described a garment for fixing a urine bag. A lot of efforts have been spent on designing similar "garments", such as in U.S. Pat. No. 4,421,509 by Schneider et al., and in U.S. Pat. No. 4,173,979 by Odis.

B. Diaper-style urine collector for adults. This category is derived from diapers for babies, and numerous patents have been written on it.

C. Urine collector specifically designed for patients. In U.S. patent application publication No. 20020143318, Flinchbaugh described a magnetic valve bladder cycler drainage system used with urinary catheters. Ahlbeck described in U.S. Pat. No. 4,421,510 a urine drainage device permitting training of the bladder. In U.S. Pat. No. 3,967,645, Gregory described a check valve for urine collection device. The valve is placed between a catheter and a urine collection bag in order to prevent back leakage. Miskie described in U.S. Pat. No. 6,679,867 a male incontinence device that uses a back flow chamber to capture urine flowing backward. Cassidy et al. invented a "soft" fluid containment bag for patients with catheters (U.S. Pat. No. 5,961,501) where hydrophilic materials are stored in the bag that gels body fluid to prevent backflow. In U.S. Pat. No. 4,747,166 by Kuntz, urine is collected in absorbent pad first, then removed to the container by a vacuum source (pump). U.S. Pat. No. 3,757,359 describes a therapeutic bed pan that collects the urine, and the urine is drained with the help of a pump for disposal. U.S. Pat. No. 2,968,046 discloses a vacuum force formed from an aspirating water jet to empty urine in a receptacle. Hadley described in U.S. Pat. No. 3,114,916 a female urine collection system with a separate vacuum source (pump). Similar ideas are seen in U.S. Pat. No. 4,360,933 and U.S. Pat. No. 4,531,939, and improvements include utilizing a urine-detecting element to activate the suction source.

D. Support system for a catheter leg bag. Various patents are described in this category for male or female patients, including U.S. Pat. Nos. 5,865,821, 3,897,785, 5,735,837, and 5,411,496.

E. Urine collector using suction force (pump). U.S. Pat. No. 3,114,916 describes a female urine collection system with a separate vacuum source (pump) mainly for bed-confined patients. U.S. Pat. No. 2,968,046 also suggests the use of a suction force (pump) to collect urine, with vacuum formed from an aspirating water jet to empty urine in a receptacle. In U.S. Pat. No. 5,894,608, Birbara designed a portable system for the collection of the urine which includes an electric motor, a fan assembly or similar suction source for providing the forced air flow required for urine entrainment. U.S. Pat. No. 6,039,060 described a way to clean urine container utilizing a venturi providing a negative pressure. U.S. Pat. No. 5,002,541 described a pump triggered by liquid sensors to draw the urine. U.S. Pat. No. 4,631,061 also described an automatic urine detecting, collecting and storing device utilizing a vacuum pump. Similar inventions were presented in U.S. Pat. Nos. 4,360,933 and 4,281,655. In U.S. Pat. No. 4,531,939, vacuum suction is used for urinating aid purpose.

F. Urine collection device designed for animals. U.S. Pat. Nos. 5,787,843 and 6,722,319 described wearable urine collection devices for animals serving an environmental protection purpose.

G. Urine collection devices designed for other special purposes. U.S. Pat. No. 6,296,627 described a device specifically for fisherman doing fly-fishing. U.S. Pat. No. 6,183,454 described a urine collection device for a female astronaut in space travel or other weightless environment alike.

H. Urine collection device with specially designed container or valve: U.S. Pat. No. 6,716,200 described an antimicrobial urine collection system. In U.S. Pat. No. 6,635,036, Tanghoej et al. designed a valve system for a collection bag. U.S. Pat. No. 6,471,680 described a Urine bag and self-retracting drain tube. U.S. Pat. No. 5,053,027 involves a female urine collection device, with a waist belt and an airtight seal. U.S. Pat. No. 4,270,539 also described a urine collection apparatus with seal and garment. In U.S. Pat. No. 5,409,474, Fleeman-Hardwick invented a waterproof non-spill valved bag for male incontinents. In U.S. Pat. No. 4,581,763, Olsen invented a container for the collection of urine and/or feces, with a non-return valve that prevents leakage.

SUMMARY

In one aspect, an apparatus is provided including a vacuum container configured to provide and substantially maintain a built-in vacuum pressure, a contact member configured to contact and substantially enclose a surface area, and a vacuum device configured to couple the built-in vacuum pressure to the surface area thereby applying a suction force on the surface area, wherein the vacuum container is also configured to retain a substance collected from adjacent the surface area.

In another aspect, an vacuum apparatus is provided including a vacuum container configured to provide and maintain a built-in vacuum pressure, a contact member configured to couple the vacuum container with a surface and substantially enclose a portion of the surface, a first valve configured to apply the built-in vacuum pressure to the portion of the surface thereby causing the contact member to apply a suction force on the portion of the surface, and a second valve configured to couple an ambient atmospheric pressure to the portion of the surface thereby releasing the portion of the surface from the suction force.

In another aspect, an apparatus is provided for collecting urine. The apparatus includes a vacuum container configured to provide and maintain a built-in vacuum pressure, a first valve configured to apply the built-in vacuum pressure, through a contact member, to a surface adjacent a urine orifice thereby applying a suction force to the surface adjacent the urine orifice, and a second valve configured to release the suction force on the surface, wherein the vacuum container is configured to directly retain the urine collected.

In another aspect, a disposable vacuum apparatus is provided including a pre-evacuated container configured to maintain a built-in vacuum pressure, a contact member configured to enclose a portion of a surface, a first valve configured to equalize a vacuum pressure in the pre-evacuated container with a pressure on the portion of the surface causing the contact member to apply a suction force on the portion of the surface, and a second valve configured to be completely closed when the contact member applies the suction force on the portion of the surface, wherein the second valve is further configured, when opened, to couple an ambient atmospheric pressure to the surface thereby releasing the portion of the surface from the suction force.

DETAILED DESCRIPTION

For travelers who are in need of a portable urine collection device, containers for other purposes are often used (such as sports drink bottles, plastic bags). Although functional, they have the problems of spillage, odor, and difficulty to dispose of.

One objective of the embodiments disclosed herein is to provide a disposable, portable and convenient to use urine collection kit for people to use in trips or in emergency when clean toilet is not readily available.

Another objective of the embodiments disclosed herein is to provide a disposable, ready-to-use vacuum source, that is, the built-in vacuum pressure in the container, which serves as a power to provide the suction force to collect urine. This suction force also provides a comfortable yet airtight seal against skins around male or female urine orifice. The same force can contain the urine and odor and prevent backflow or spillage.

Just as carbonated drink bottles or cans that hold a "positive" pressure, an apparatus in accordance with embodiments disclosed herein can maintain a "negative," or vacuum pressure. The term "vacuum" in the present application has its ordinary meaning, "capable of creating a differential pressure," "isolated," or "a state of being sealed off from external or environmental influences." The material or structure of the apparatus is configured to maintain such a negative pressure. It is foreseeable that the cost of such a vacuum container is comparable to a soda can or bottle.

Figure 1:
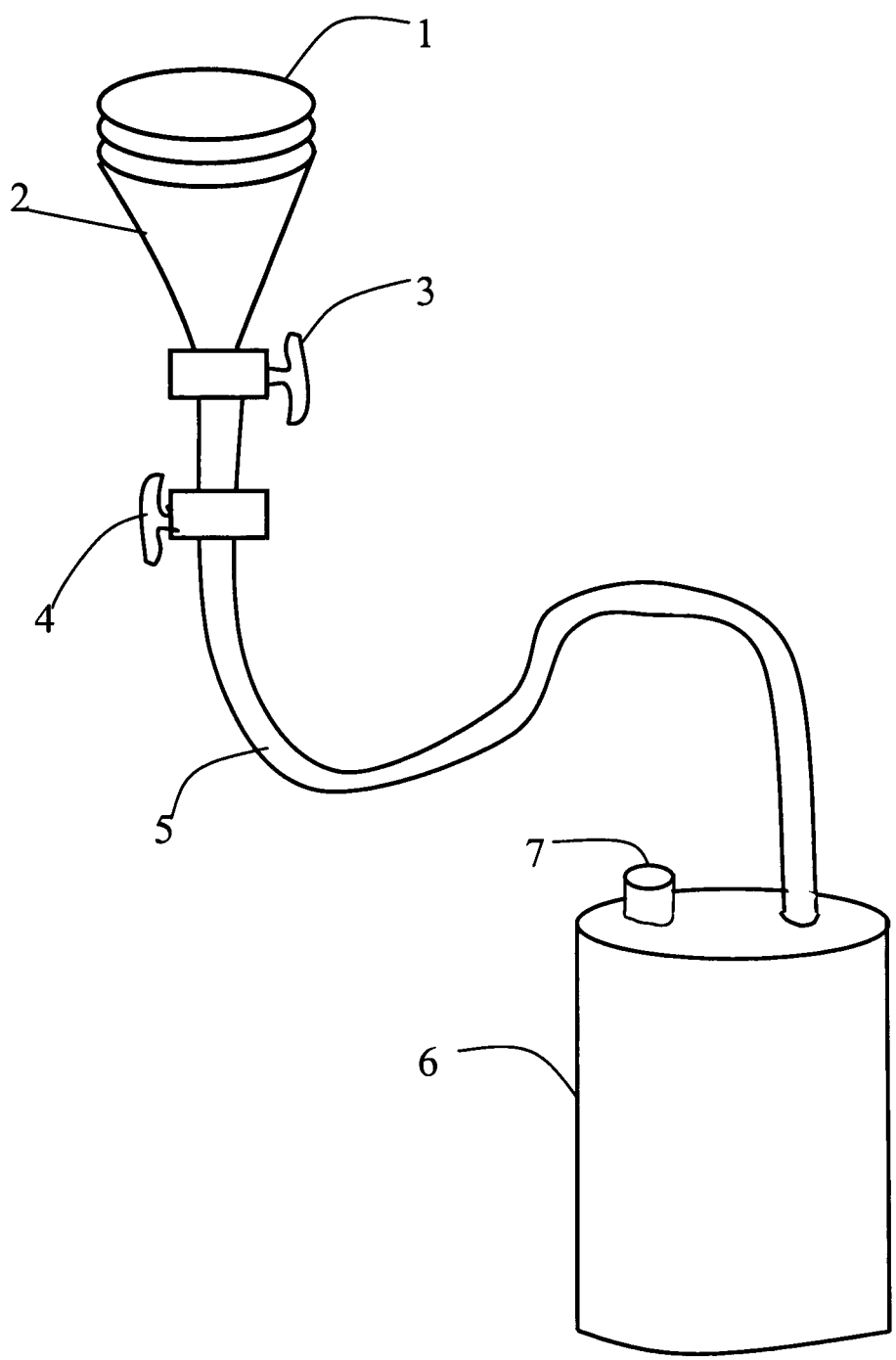
FIG. 1 illustrates a disposable urine collection kit in accordance with embodiments of the present invention.

FIG. 1 illustrates a urine collection kit in accordance with some embodiments, wherein a ring-shaped vacuum seal 1 is used for a female urine orifice. A lower part of an extendable funnel 2 is configured to seal a male penis. A valve 3 is used to connect the funnel 2 with the ambient atmosphere to release the vacuum pressure inside the funnel 2, thus releasing the suction force on the skins. A valve 4 connects the funnel 2 with a tube 5 and a container 6. A removable cap 7 may be used to dump or collect the urine and pump out the air for a possible reuse of the kit.

When used as a urine collection kit, the apparatus as illustrated in FIG. 1 may have the funnel work as a receptacle connected to the container that maintains a built-in vacuum pressure. In the case of a solid container illustrated in FIG. 1, the vacuum pressure is supported by the tension of the container wall. In the case of a collapsible container, the built-in vacuum pressure may be supported by a reusable supporting structure. The built-in vacuum pressure serves as a means to collect urine, to prevent spillage of the fluid, and to help contain the odor within the container. The apparatus provides a suction force for a comfortable yet airtight seal between the receptacle and a urinating organ of a male or female user. The apparatus is stored with the container maintaining a vacuum pressure. When in use, after fitting the receptacle with skins around the urine outlet, the valve 4 connecting the receptacle and the container is opened. Thus, the receptacle, the connecting tube, and the container are connected with the same built-in vacuum pressure, supported by the tension from the container wall or from the supporting structure. After usage, the valve 4 is closed to isolate the tube and the container, which still maintain a pressure lower than the ambient atmospheric pressure thus retaining the liquid as well as the odor. The valve 3 is then opened to connect the receptacle with the ambient atmosphere, thus releasing the receptacle from the vacuum pressure. The entire kit, except the optional re-usable supporting structure, can be disposed or recycled or utilized for extracting useful chemicals from the urine.

Figure 2:
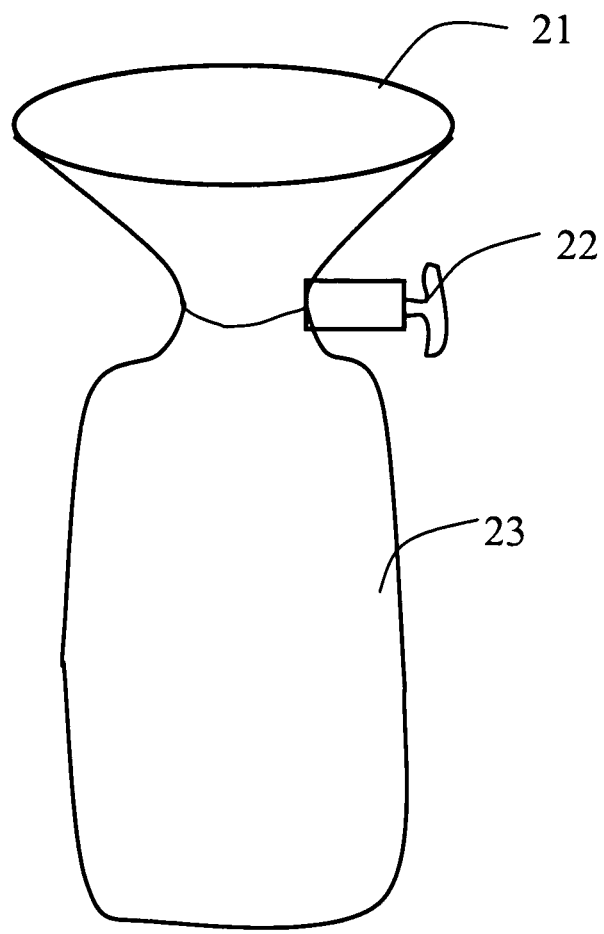
FIG. 2 illustrates an apparatus providing a suction force to be used in physical therapy.

FIG. 2 illustrates an embodiment that may be used as a tool for physical therapy. A vacuum seal 21 may be used for skin contact. The size of the opening of the seal 21 is determined by the purpose of usage. A small opening applying suction force on a small area of skin may be used to treat skin acne. A large opening can be used for physical therapy. A valve 22 connects a vacuum container 23 with the vacuum seal 21. When the valve 22 is opened, the vacuum suction force is applied to the skin in contact with the seal 21. The ratio between the volume of the container 23 and the volume contained between the skin and the vacuum seal 21 determines the suction force applied.

In one preferred embodiment, a collapsible container has a restoring tension provided by external spring-like structure, and the restoring tension provides the suction force.

The examples disclosed herein are for illustrative purpose only and should not be interpreted to be limiting. Those skilled in the art will recognize that other alternative embodiments are possible to implement the essential ideas of disclosed herein.

Three examples of alternate embodiments include: (1) A solid plastic bottle with a built-in vacuum pressure. The bottle cannot be collapsed. This may provide the strongest vacuum pressure but needs more storage space. (2) A collapsed plastic bottle. The container structure is manufactured such that it has a built-in tension from skeleton-like structures to recover the shape of the container to a non-collapsed state, thus providing the suction force. (3) A collapsed container with a supporting structure. The supporting structure can be made with stainless steel or materials alike with a strong tension that supports the sucking force of the container. The supporting structure can be re-used as it does not have contact with the urine.

A vacuum pump may be provided to users who prefer to reuse the kit. The pump can be connected to the removable cap of the container, and pump the container to a certain vacuum level.

The pump can be an either electrical or manual pump, with the output vacuum pressure adjustable according to users' comfort level.

Other applications of the various embodiments include a universal disposable vacuum source that can be applied to other areas of applications. For example, in traditional Chinese medicine, a suction force is needed to apply to acupressure points on the patients, to achieve effects similar to acupuncture. The suction force has been achieved by setting fire in a small container placed on the patient's skin corresponding to the acupressure points, followed by a procedure of applying a small pot to cover the fire. The fire burns out oxygen in the small pot and causes a suction force from the partial vacuum. In this procedure, there is an obvious hazard of fire and a difficulty in controlling the strength of the suction force. Using the canned vacuum source in accordance with embodiments disclosed herein, one can easily apply plastic cans of various sizes and vacuum pressure of different strengths on the patient. The cans can be disposable to save the cost of disinfections.

Another method of using embodiments in accordance with embodiments disclosed herein is to manufacture small plastic tubes with built-in vacuum, which can be used in skin care industry to provide a clean, ease-to-use, and disposable source of suction force to treat acne and to extract secretions from skin follicles.

Another method of using embodiments in accordance with embodiments disclosed herein is to manufacture vacuum cans with various sizes that can be applied to patient skins after plastic surgery to help maintain the desired shape of the patient body, or to collect secretions after the surgery, or to use as a tool for physical therapy.

Advantages of embodiments disclosed herein include one or more of the following: (a) a low-cost one-time vacuum source that can have many applications; (b) when used as a disposable urine collection kit, the built-in vacuum pressure helps retain the urine and the odor; (c) the strength of the suction force can be designed and manufactured based on the vacuum pressure level, which in turn is determined by the material and structural design of the container.

While the invention has been described with respect to a limited number of embodiments, those of ordinary skill in the art, having benefit of this disclosure, will appreciate that other embodiments can be advised which do not depart from the scope of the invention as disclosed herein. For example, the "valve" in this disclosure will be recognized by one or ordinary skill in the art that it may be any types of valves to isolate and to connect the built-in vacuum with the ambient atmospheric pressure, and the container may be made of any types of materials or structures as long as it has sufficient strength to retain the built-in vacuum pressure. Accordingly, the scope of the invention should be limited only by the attached claims.

What is claimed is:

1. An apparatus, comprising:
   a vacuum container configured to provide and substantially maintain a built-in vacuum pressure;
   a contact member configured to contact and substantially enclose a surface area; and
   a vacuum device configured to couple the built-in vacuum pressure to the surface area thereby applying a suction force on the surface area;
   wherein the vacuum container is also configured to retain a substance collected from adjacent the surface area,
   wherein the vacuum container comprises a collapsible container, and
   wherein the collapsible container comprises a spring member configured to maintain a tension in a wall of the vacuum container.

2. The apparatus of claim 1, wherein the vacuum container is configured to retain a liquid substance collected from adjacent the surface area.

3. The apparatus of claim 1, wherein the vacuum apparatus is reusable by re-evacuating the vacuum container.

4. The apparatus of claim 1, wherein the contact member comprises an extendable funnel.

5. The apparatus of claim 1, wherein the apparatus is disposable.

6. The apparatus of claim 1, wherein the contact member comprises a vacuum seal.

7. The apparatus of claim 1, wherein the contact member comprises a ring-shaped vacuum seal.

8. The apparatus of claim 1, wherein the vacuum device is further configured to release the vacuum pressure on the surface area.

9. The apparatus of claim 1, wherein the vacuum device is further configured to isolate the vacuum container from an ambient atmospheric pressure.

10. The apparatus of claim 1, wherein the vacuum device comprises a first vacuum valve configured to equalize the built-in vacuum pressure with the pressure on the surface area.

* * * * *